United States Patent
Parkins (10) Patent No.: US 10,448,143 B2
(45) Date of Patent: *Oct. 15, 2019

(54) WIRELESS COMMUNICATIONS HEADSET SYSTEM EMPLOYING A LOOP TRANSMITTER THAT FITS AROUND THE PINNA

(71) Applicant: Red Tail Hawk Corporation, Philadelphia, PA (US)

(72) Inventor: John W. Parkins, Ithaca, NY (US)

(73) Assignee: Red Tail Hawk Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/138,603

(22) Filed: Apr. 26, 2016

(65) Prior Publication Data

US 2016/0241959 A1  Aug. 18, 2016

Related U.S. Application Data

(63) Continuation of application No. 14/179,884, filed on Feb. 13, 2014, now Pat. No. 9,351,064, which is a
(Continued)

(51) Int. Cl.
*H04R 3/04* (2006.01)
*H04R 1/10* (2006.01)
(Continued)

(52) U.S. Cl.
CPC ............ *H04R 1/1091* (2013.01); *A61F 11/08* (2013.01); *H01Q 1/273* (2013.01); *H01Q 7/08* (2013.01);
(Continued)

(58) Field of Classification Search
None
See application file for complete search history.

(56) References Cited

U.S. PATENT DOCUMENTS 2,048,604 A  7/1936 Finch
2,268,665 A  1/1942 Loewe
(Continued)

FOREIGN PATENT DOCUMENTS

DE  3508830 A1  9/1986
DE  3826294 A1  2/1990
WO  2006042298 A2  4/2006

OTHER PUBLICATIONS

Knowles Acoustic ED Series Speaker Specification. Dec. 2003.
(Continued)

*Primary Examiner* — Qin Zhu
(74) *Attorney, Agent, or Firm* — Brown & Michaels, PC (57) ABSTRACT

A wireless communications headset system for double hearing protection systems that eliminates the problems associated with typical wireless communications systems. The system employs a magnetic-field coupled wireless link from a loop transmitter to a magnetic field receiver. Current through the transmitter wire loops generates magnetic flux which passes through a communications earplug. The earplug has a receiver for converting the magnetic flux to electrical voltage, and this voltage is used to drive a speaker within the earplug. The transmitter can be easily installed into aviation headsets. The loop transmitter has an open center sized so that it fits around the pinna of the human ear enabling a close position to the communications earplug. This close position is advantageous if an efficient system is desired.

19 Claims, 7 Drawing Sheets

Related U.S. Application Data continuation of application No. 11/837,129, filed on Aug. 10, 2007, now Pat. No. 8,688,036.

(60) Provisional application No. 60/824,091, filed on Aug. 31, 2006.

(51) Int. Cl.

| | | |
|---|---|---|
| *H04R 1/08* | (2006.01) | |
| *A61F 11/08* | (2006.01) | |
| *H04M 1/05* | (2006.01) | |
| *A61F 11/14* | (2006.01) | |
| *H04M 1/215* | (2006.01) | |
| *H01Q 1/27* | (2006.01) | |
| *H01Q 7/08* | (2006.01) | |

(52) U.S. Cl.
CPC ............... *H04M 1/05* (2013.01); *H04R 1/08* (2013.01); *H04R 1/1016* (2013.01); *H04R 1/1083* (2013.01); *H04R 3/04* (2013.01); *A61F 11/14* (2013.01); *H04M 1/215* (2013.01); *H04R 2201/107* (2013.01); *H04R 2420/07* (2013.01)

(56) References Cited

U.S. PATENT DOCUMENTS

| | | | |
|---|---|---|---|
| 2,530,621 | A | 11/1950 | Lybarger et al. |
| 3,125,646 | A | 3/1964 | Lewis |
| 3,322,897 | A | 5/1967 | Vozeolas et al. |
| 3,752,939 | A | 8/1973 | Bartz |
| 4,150,262 | A | 4/1979 | Ono |
| 4,957,478 | A | 9/1990 | Maniglia |
| 4,972,491 | A | 11/1990 | Wilcox, Jr. |
| 5,073,947 | A | 12/1991 | Reddemann et al. |
| 5,343,532 | A | 8/1994 | Shugart, III |
| 5,396,563 | A | 3/1995 | Yoshimi |
| 5,420,930 | A | 5/1995 | Shugart, III |
| 5,701,348 | A | 12/1997 | Shennib et al. |
| 5,748,754 | A * | 5/1998 | Maag .................. H03G 5/025 381/101 |
| 5,796,821 | A | 8/1998 | Crouch et al. |
| 6,012,812 | A | 1/2000 | Rickards |
| 6,078,675 | A | 6/2000 | Bowen-Nielsen et al. |
| 6,208,740 | B1 | 3/2001 | Grever |
| 6,438,245 | B1 | 8/2002 | Taenzer et al. |
| 6,694,034 | B2 | 2/2004 | Julstrom et al. |
| 6,823,171 | B1 | 11/2004 | Kaario |
| 6,925,179 | B2 | 8/2005 | Waldron et al. |
| 7,206,426 | B1 | 4/2007 | Julstrom et al. |
| 7,426,279 | B2 | 9/2008 | Cochran et al. |
| 8,116,494 | B2 | 2/2012 | Rass |
| 2002/0061113 | A1 | 5/2002 | van Halteren et al. |
| 2002/0141545 | A1 | 10/2002 | Segovia |
| 2003/0031339 | A1 | 2/2003 | Marshall et al. |
| 2003/0108209 | A1 * | 6/2003 | McIntosh ............... H03G 5/005 381/74 |
| 2003/0219135 | A1 | 11/2003 | Morimoto |
| 2004/0151334 | A1 | 8/2004 | Vaudrey et al. |
| 2004/0213430 | A1 | 10/2004 | Stiles |
| 2004/0258261 | A1 | 12/2004 | Cochran et al. |
| 2005/0018859 | A1 | 1/2005 | Buchholz |
| 2005/0078848 | A1 | 4/2005 | Hlibowicki |
| 2005/0094830 | A1 | 5/2005 | Stanley |
| 2005/0178835 | A1 | 8/2005 | Akiho |
| 2005/0245213 | A1 | 11/2005 | Hirano et al. |
| 2005/0260953 | A1 | 11/2005 | Lefler et al. |
| 2006/0013420 | A1 | 1/2006 | Sacha |
| 2006/0269088 | A1 | 11/2006 | Julstrom et al. |
| 2007/0041602 | A1 | 2/2007 | Killion |
| 2007/0041606 | A1 | 2/2007 | Sheppard |
| 2007/0149261 | A1 | 6/2007 | Huddart |
| 2007/0153444 | A1 | 7/2007 | Groh et al. |
| 2008/0025524 | A1 | 1/2008 | Vaudrey et al. |
| 2008/0132193 | A1 | 6/2008 | Petrovic et al. |
| 2009/0015197 | A1 | 1/2009 | Sogabe |
| 2009/0041285 | A1 | 2/2009 | Parkins et al. |
| 2009/0143097 | A1 | 6/2009 | Wilson |
| 2010/0016827 | A1 | 1/2010 | Hunter et al. |
| 2010/0278371 | A1 | 11/2010 | Hanada |
| 2010/0296667 | A1 | 11/2010 | Parkins |
| 2011/0081936 | A1 | 4/2011 | Haim et al. |
| 2011/0103605 | A1 | 5/2011 | Killion et al. |
| 2011/0130622 | A1 | 6/2011 | Ilberg |
| 2012/0021704 | A1 | 1/2012 | Chan et al. |
| 2012/0161549 | A1 | 6/2012 | Sell |
| 2012/0275638 | A1 | 11/2012 | Chang |
| 2012/0322378 | A1 | 12/2012 | Tai |
| 2013/0244722 | A1 | 9/2013 | Rousu et al. |
| 2014/0087659 | A1 | 3/2014 | Parkins |
| 2014/0177863 | A1 | 6/2014 | Parkins |
| 2014/0295909 | A1 | 10/2014 | Ouchi et al. |
| 2015/0380821 | A1 | 12/2015 | Parkins |
| 2017/0104262 | A1 | 4/2017 | Parkins |

OTHER PUBLICATIONS

Viking Chip Common Mode Choke-CM Series. Apr. 2006.
Van Wiljngaarden et al. "Development of the Wireless "Communications Earplug" for application in Military Aviation" J. Audio Eng. Soc., vol. 48, No. 6, Jun. 2000.
Van Wijngaarden et al. "Protecting Crew Members against Military Vehicle Noise." Presented at the RTO AVT Symposium and published in RTO-MP-AVT-110; pp. 1-18; Oct. 2004.
SJSU "Electromagnetic Induction", http://www.physics.sjsu.edu/becker/physics51/induction.htm; Jan. 2007.

* cited by examiner

WIRELESS COMMUNICATIONS HEADSET SYSTEM EMPLOYING A LOOP TRANSMITTER THAT FITS AROUND THE PINNA

REFERENCE TO RELATED APPLICATIONS

This application is a continuation of co-pending application Ser. No. 14/179,884, entitled "Wireless Communications Headset System Employing a Loop Transmitter That Fits Around The Pinna", filed on Feb. 13, 2014, which was a continuation of application Ser. No. 11/837,129, entitled "Wireless Communications Headset System Employing a Loop Transmitter That Fits Around The Pinna", filed on Aug. 10, 2007, which issued on Apr. 1, 2014, as U.S. Pat. No. 8,688,036, which claimed benefit under 35 USC §119(e) of Provisional Application No. 60/824,091, filed Aug. 31, 2006, entitled "Wireless Communications System Employing a Loop Transmitter That Fits Around The Pinna". The aforementioned applications are hereby incorporated herein by reference.

ACKNOWLEDGMENT OF GOVERNMENT SUPPORT

This invention was made with Government support under SBIR Contract No. N68335-03-C-0249, awarded by the US Navy. The government has certain rights in the invention.

BACKGROUND OF THE INVENTION

Field of the Invention

The invention pertains to the field of sound transducers. More particularly, the invention pertains to earphones for communications devices.

Description of Related Art

It is well documented in literature that the use of double hearing protection (earmuff and earplug) is superior in providing noise attenuation compared to using only one hearing protection device alone. Often communications are also necessary, and thus, a communications earplug is used.

U.S. Pat. No. 4,972,491, "Ear-Mic Headseat/Eardefender" shows such an arrangement where earplugs within earmuffs/headset are hard-wired to headset cord. This is discussed in the June, 2000, issue of the Journal of the Audio Engineering Society in an article entitled "Development of the Wireless Communications Earplug for Application in Military Aviation (Van Wijngaarden et al, *J. Audio Eng. Soc.*, Vol. 48, No. 6, pp. 553-558).

The problem with typical communications earplugs is that they employ wires to provide the communications signal, and the problems with using wires are manifold.

Inductive coupling for communications is known to the art. For example, see U.S. Pat. No. 2,268,665, "Method and Arrangement for Transferring Telephone Conversations to Other Electrical Devices" which is a cradle for telephone handset which picks up sound by inductance, or U.S. Pat. No. 3,322,897, "Coil Pick-up and Tube Recorder System" which uses circular loop pickup around handset earpiece to pick up telephone signals for a recorder.

Inductive coupling is commonly used between a telephone handset and a hearing aid. This application is often referred to as a "T-coil". For examples, see U.S. Pat. No. 2,530,621, "Wearable Hearing Aid with Inductive Pick-Up for Telephone Reception", or U.S. Pat. No. 5,796,821, "Hearing aid telephone interconnect system".

U.S. Pat. No. 3,125,646, "Electromagnetically Coupled Hearing Aid" couples an amplified signal from a sound input unit in eyeglasses or headband to a sound output unit in user's ear.

U.S. Pat. No. 5,420,930, "Hearing aid device" uses a receiver assembly having a flexible coil shape worn in the outer portion of the auditory canal with a small transducer that extends into the auditory canal, and a transmitter assembly. The receiver is driven by magnetic induction from the transmitter assembly positioned a few inches away, as in a neck pendant. Similarly, in U.S. Pat. No. 6,208,740, "Stereophonic magnetic induction sound system" the user wears a necklace with transmitter which transmits sound inductively to active receiver units in ears.

US Published Patent Application 2004/151,334, "Actuator for an active noise control system" is an in-ear transducer for use in ANR system with several embodiments, all including permanent magnets, diaphragms and voice coils.

US Published Patent Application 2005/18,859, "Optically Driven Audio System" shows an alternate system of earmuffs/in-ear earplug using optical transmission from transmitters to active receivers.

SUMMARY OF THE INVENTION

The invention comprises a wireless communications headset system for double hearing protection systems that eliminates the problems associated with typical wireless communications systems. The system employs a magnetic-field coupled wireless link from a loop transmitter to a magnetic field receiver. Current through the transmitter wire loops generates magnetic flux which passes through a communications earplug.

The earplug has a receiver for converting the magnetic flux to electrical voltage, and this voltage is used to drive a speaker within the earplug. The transmitter can be easily installed into aviation headsets. The loop transmitter has an open center sized so that it fits around the pinna of the human ear enabling a close position to the communications earplug. This close position is advantageous if an efficient system is desired. In addition, a transmitter surrounding a receiver results in less sensitivity change as a function of position. The magnetic field strength within a coil is uniform compared to the field strength as one moves away from a coil, hence, the system will sound similar in loudness even if the transmitter is shifted side-to-side or up and down. Moreover, a transmitter that surrounds the pinna will not interfere with the pinna during side impacts to a headset. The size and location of the transmitter also enables one to use typical headset speakers in conjunction with the transmitter as a redundant communications system if desired.

DETAILED DESCRIPTION OF THE INVENTION

The present invention is a wireless communications system for double hearing protection systems that eliminates the problems associated with typical wireless communications systems. It provides attenuation of ambient acoustic noise while providing communications to the user by using an earmuff in conjunction with a communications earplug. The earplug employs a miniature speaker for communications purposes. The earmuffs can be part of a headset, such as an aviation headset for pilots which has a pair of earmuffs, a headband to hold the earmuffs in place, and a boom microphone for transmission. The earmuffs could also be built into a pilot's helmet or similar headgear.

The system uses a magnetic-field coupled wireless link from a loop transmitter in the earmuff that is sized to fit around the pinna of the ear to a magnetic field receiver in the earplug. Current through the transmitter wire loops generates magnetic flux which passes through a communications earplug. The earplug has a receiver for converting the magnetic flux to electrical voltage, and this voltage is used to drive a speaker within the earplug.

One version of the receiver consists of loops of wire wrapped around the speaker, which results in a very compact design. In addition, if magnetic material is placed within the receiver coils with the speaker, higher efficiency is achieved. If the speaker uses magnetic material in its construction, this magnetic material will improve the efficiency of the receiver as well.

Loop Transmitter

Figure 1:
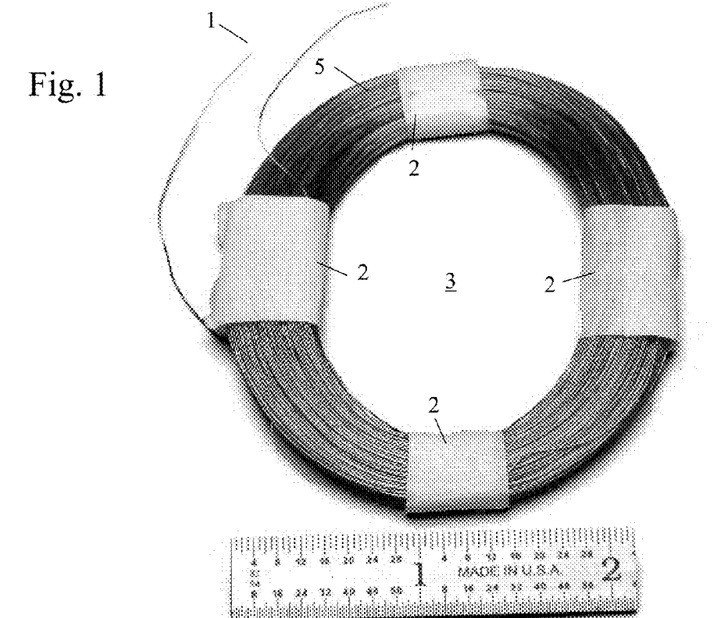
FIG. 1 shows a loop transmitter.

One version of the loop transmitter can be seen in FIG. 1. The transmitter (1) shown in the figure is made in the form of a loop (5) using 550 turns of 34 gauge wire, but other turns/gauge configurations can be used to set the desired input impedance of the device. Four pieces of tape (2) are holding the wire loop (5) in place in this example.

The transmitter (1) generates a high magnetic flux field within the space (3) inside of the loop (5) in a direction normal to the plane of the transmitter coils, that is, down through the inner area (3) of the coils.

Figure 2:
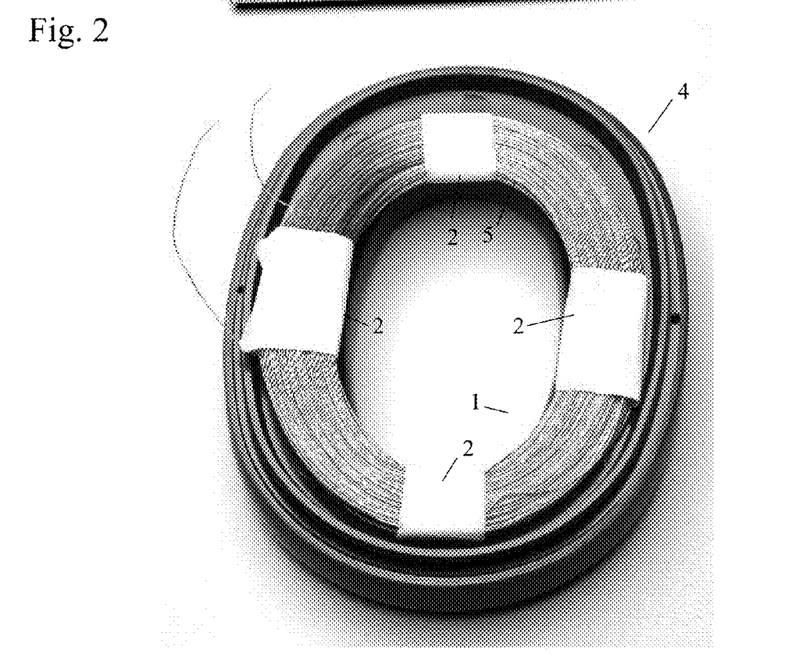
FIG. 2 shows a loop transmitter resting on back side of earcup cushion.

This version of the transmitter (1) is mounted behind the ear cushion (4) of an earmuff as shown in FIG. 2. Ear cushions (4) are designed to fit around the ear, so the opening (3) of the cushion (4) must be large enough that an ear can fit within. The transmitter here is of a size and shape that it will also allow the ear to fit within and has generally the same size opening as the ear cushion (4).

Figure 3:
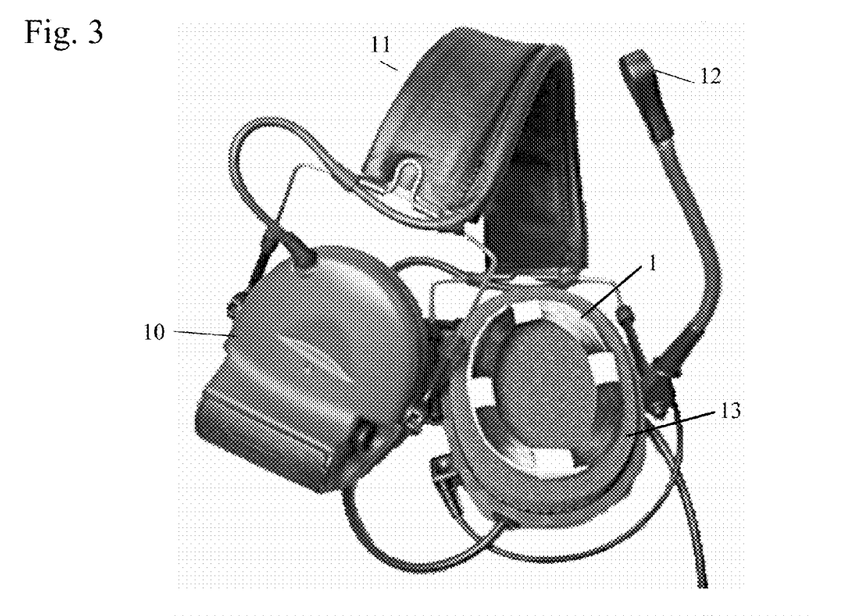
FIG. 3 shows a headset with ear cushion removed showing placement of loop transmitter.
Figure 4:
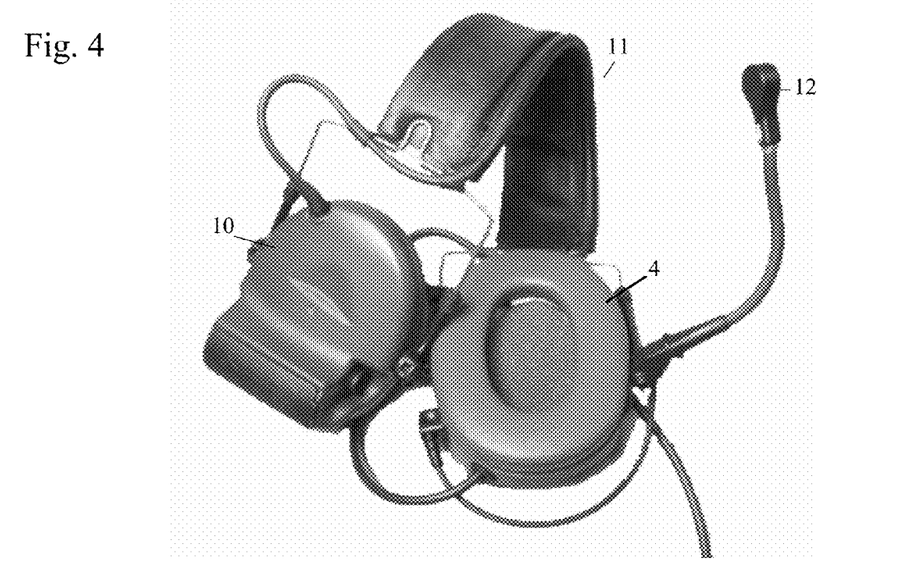
FIG. 4 shows a headset with loop transmitter mounted behind ear cushion.

The loop transmitter (1) resting on the inner foam of a headset (11) earcup or earmuff (10) with the cushion removed can be seen in FIG. 3, while FIG. 4 shows the same headset (11) with loop transmitter (1) but with the ear cushion (4) mounted. It can be seen that the transmitter (1) has the same size opening as the ear cushion (4) and would allow room for an ear when the headset (11) is worn. A communications speaker located behind damping foam (13) does not mechanically interfere with the loop transmitter (1). The communications speaker can be used as a backup system in case the wireless system fails.

The coils of the loop transmitter can be wrapped around a bobbin, made of plastic or other material, to facilitate the winding process. This bobbin may be used as a mechanical structure to hold the loops in place when the transmitter is mounted to a mechanical object such as an ear cushion.

Figure 5:
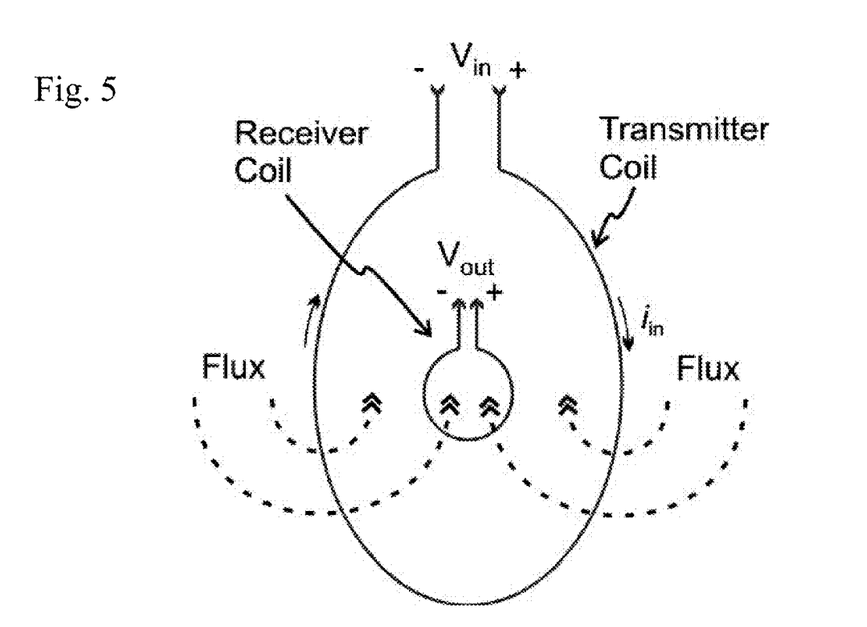
FIG. 5 shows schematically how voltage input to the loop transmitter generates a current.

FIG. 5 is a simplified schematic illustration of the fundamental mechanism by which the loop transmitter generates a magnetic field. It will be understood that the loop transmitter may employ multiple turns or a single turn, but a coil or loop of only one turn is shown here for clarity.

A voltage, $V_{in}$, input to the wire of the transmitter coil results in a current, $i_{in}$, through the coil. This current generates magnetic flux that circulates around the wire which results in flux passing through the space within the loop coils. A receiver coil (again shown as only one turn for clarity), located within the transmitter coil, can be used to sense the magnetic flux and generate a voltage, $V_{out}$. This voltage can be used to drive a speaker located in a communications earplug.

Receiver

The receiver used in this wireless system can consist of a loop antenna with or without a magnetic core, although other antenna designs may be used.

Figure 6:
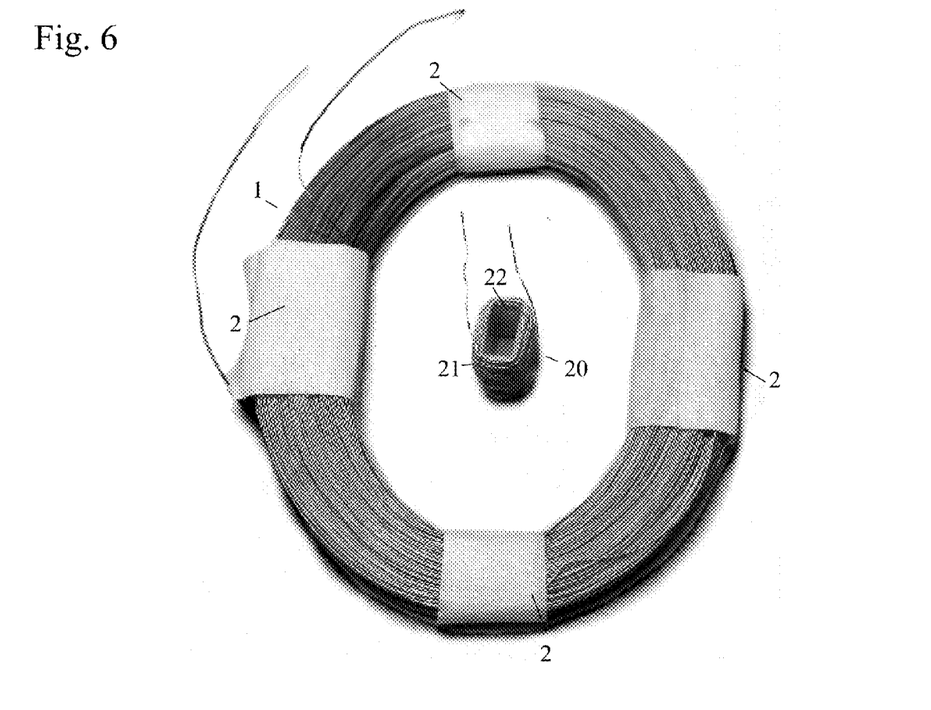
FIG. 6 shows a loop transmitter with receiver coil in the center.

FIG. 6 shows the loop antenna receiver (20), located in the center of the transmitter loop (1). The coils (21) of the loop antenna receiver (20) may be wound upon a receiver core (22), which will produce a higher output if a magnetic material (such as magnetic ceramic or various metal alloys among other materials) is located within its interior.

Many hearing aid speakers use a magnetic material for their casing to magnetically shield the inner workings of the speaker. To make the receiver/speaker combination very compact, the speaker itself can be placed within the coils' interior.

Hearing aid speakers such as those manufactured by Knowles or Sonion would be appropriate for this application.

Figure 7:
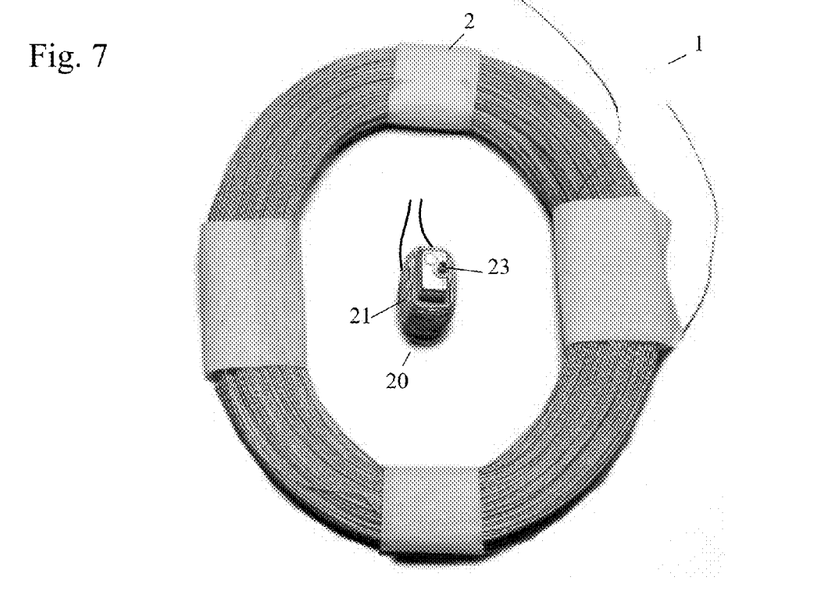
FIG. 7 shows a loop transmitter with receiver coils wrapped around speaker.

A loop antenna receiver (20) with miniature speaker (23) installed within its center is shown in FIG. 7. The magnetic flux generated by the loop transmitter (1) flows through the inner area of the transmitter and through the coils (21) of the receiver (20) which generates a voltage. The speaker (23) need not be placed within the receiver coils (21), but this configuration results in a more compact design.

No battery is needed in this receiver design.

Figure 8:
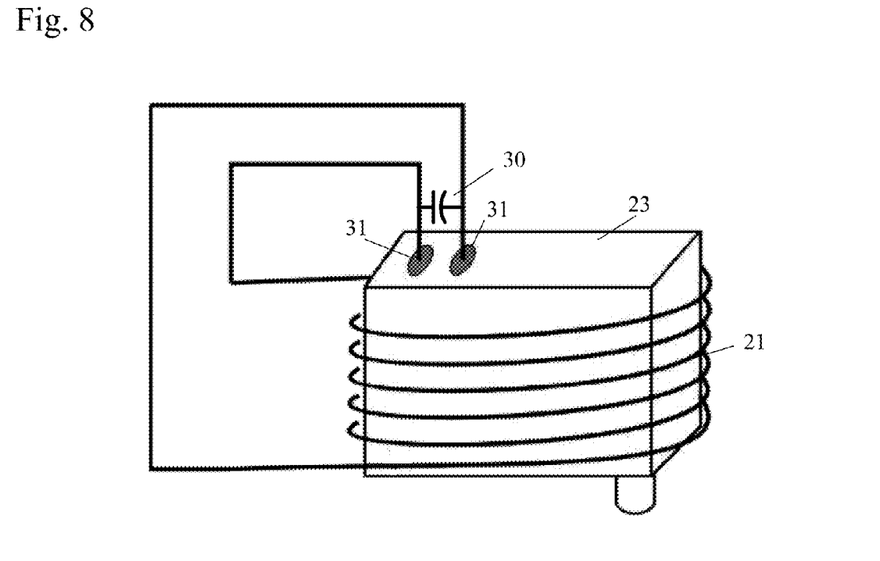
FIG. 8 shows a speaker located within the receiver coils.

In FIG. 8, a speaker (23) is shown positioned within the receiver coil (21) as described earlier.

Hearing aid speakers are often shielded—if the speaker's casing is made of magnetic material, the location of the speaker serves to increase the output of the receiver. If a speaker with magnetic casing is used, the high permeability of the casing tends to focus the flux lines through the center of the receiver coils. If the speaker casing is not made of magnetic material, magnetic material can be placed within the receiver coil (21) along with the speaker (23). In addition, the speaker may be placed at some other location and not within the receiver coils (21).

The voltage generated by the receiver coil (21) can be input to the terminals (31) speaker (23) directly, as shown in the figure. Additionally, the output voltage from the coils can drive an equalization circuit or other electronic circuit to tailor the frequency response of the system. This circuit may in turn drive the speaker. For example, a chip capacitor (30) can be connected across the terminals (31), as shown in FIG. 8 to increase the response of the system at mid frequencies. Moreover, if the magnetic field is a modulated field, such as (but not limited to) a radio frequency amplitude modulated field, the receiver may employ a passive demodulator. Such demodulators may consist of a diode (for rectifying the signal), a tuning capacitor (for tuning the circuit), and a filter capacitor (for filtering out high frequency components).

Communications Earplug

Figure 9:
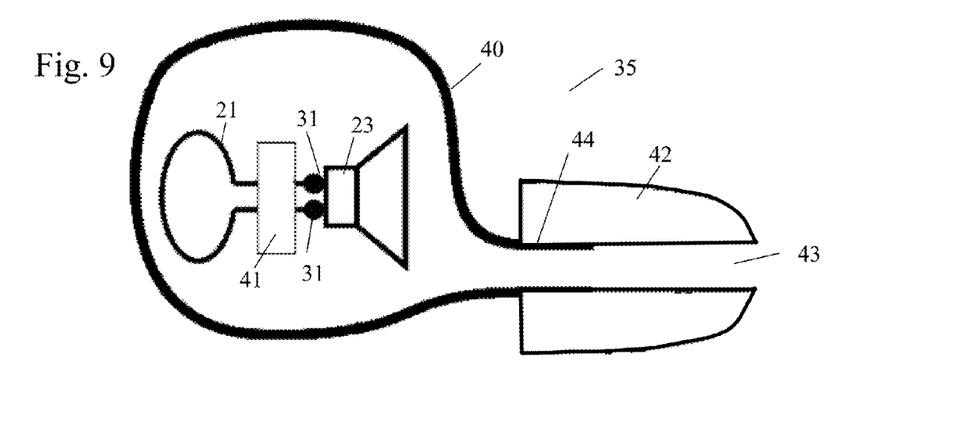
FIG. 9 shows a drawing of communications earplug with magnetic field receiver.

A representation of a communications earplug (35) with the loop receiver can be seen in FIG. 9.

The speaker (23) and loop receiver (21) are located within the earshell (40) of the communications earplug. The output of the loop receiver is input to an electronic equalization and/or demodulator circuit (41). The output of this circuit (41) is connected to the terminals (31) of the speaker (23) to produce sound in the eartip (42).

The earplug in this example employs a foam removable eartip (42). The eartip (42) forms an acoustic seal with the ear canal, thereby providing ambient noise attenuation. The eartip (42) is mounted to the earplug nipple (44). Through the center of the eartip (42) is a sound delivery tube (43) which provides an acoustic path for sound from the speaker (23) to reach a user's ear canal.

Figure 10:
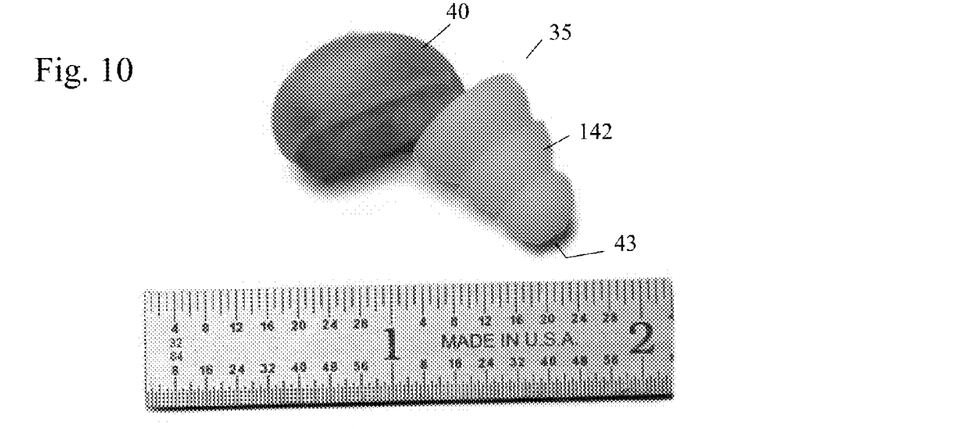
FIG. 10 shows a wireless communications earplug.

In FIG. 10 an earplug (40) can be seen that employs a rubber flanged eartip (142) as opposed to a foam eartip. Eartips made of many different materials and sizes can be used in this design.

Figure 11:
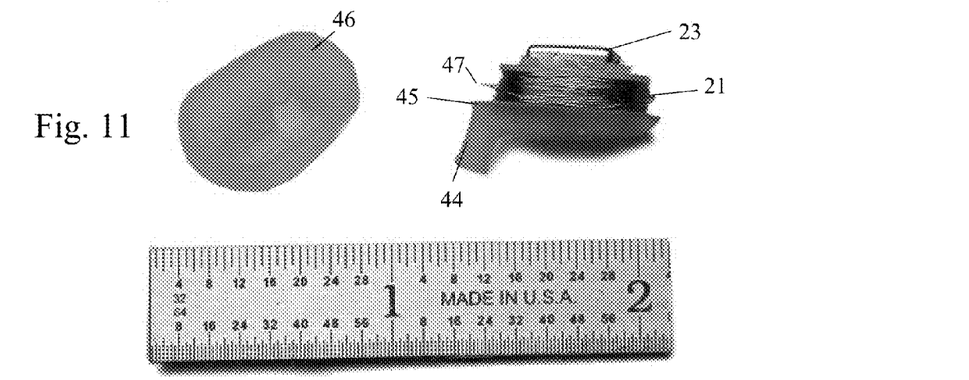
FIG. 11 shows an interior of a communications earplug employing loops of wire wrapped around a speaker.

In FIG. 11 the cover (46) of the earshell (40) of the earplug (35) is removed from the rest of the earshell body (45), showing loops of wire (21) wrapped around the speaker (23) as a receiver. The wires (47) of the receiver coil would be attached to the speaker (23), but are not connected in this view. The eartip (42) would be connected over the nipple (44), but is also not shown in this view.

Figure 12:
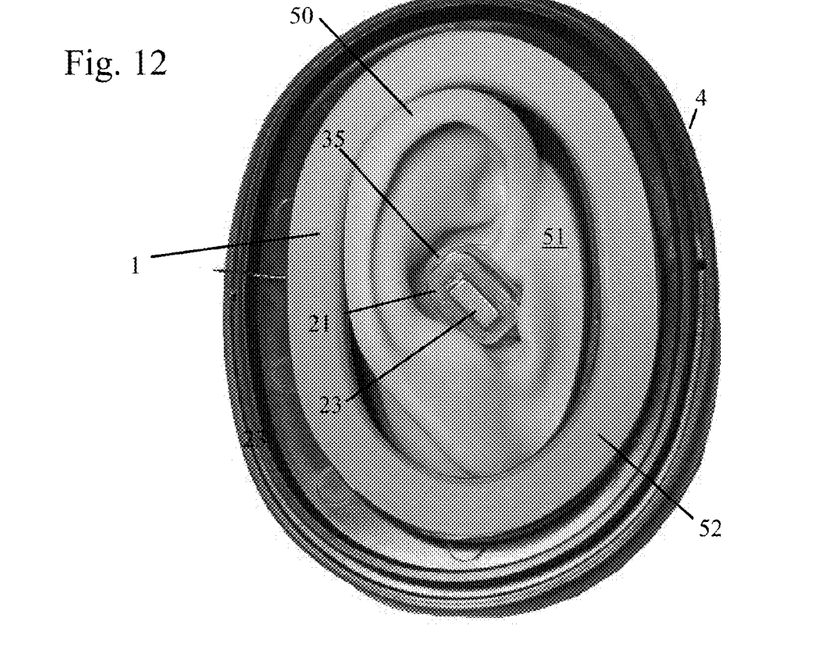
FIG. 12 shows an example of a loop transmitter with communications earplug.

The communications earplug, as worn on an ear (51), can be seen in FIG. 12. The coil (1) of the transmitter is wound onto a plastic bobbin (52), which is mounted to the back side of an ear cushion (4) of a headset (not shown.) The earplug (35) with receiver is generally located within the coil (1) of the transmitter. This makes for a highly efficient design. The earplug cover is removed in this figure, exposing the receiver coil (21) and speaker (23) locations. The transmitter is located behind the ear cushion (4) of a headset (not shown).

The ear cushion (4) and transmitter coil (1) both fit around the pinna (50) of an ear (51). The location of the transmitter around the ear (51) results in a system with high sensitivity, to the point where batteries are not even necessary to power the system if an audio signal is directly input to the transmitter. The voltage from the audio signal of a typical military radio can drive the transmitter to achieve sufficient output at the receiver and audio output in the ear canal when a transmitter of this design is used.

Figure 13:
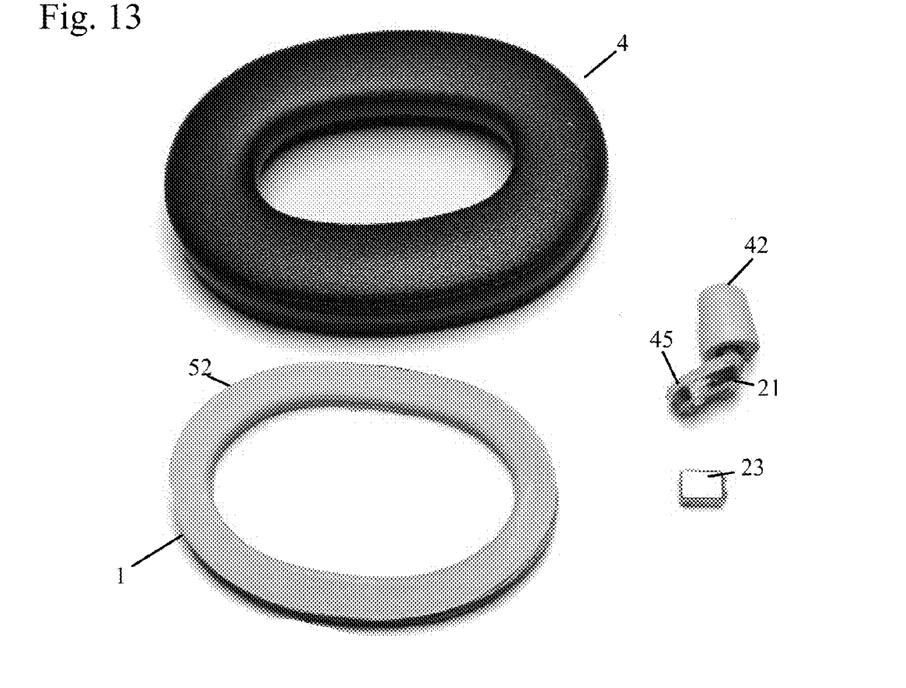
FIG. 13 shows individual components from FIG. 12.

The individual components shown in FIG. 12 can be seen in better detail in FIG. 13.

Figure 14:
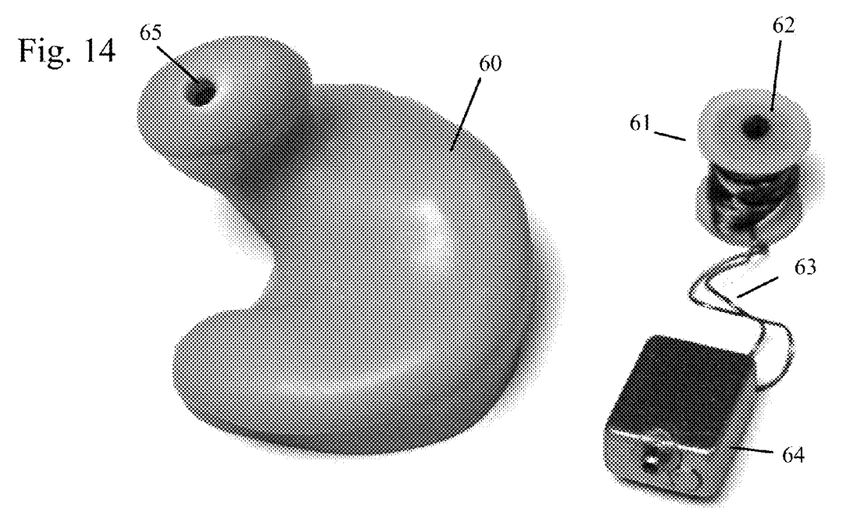
FIG. 14 shows an embodiment of the earplug with a molded earshell
Figure 15:
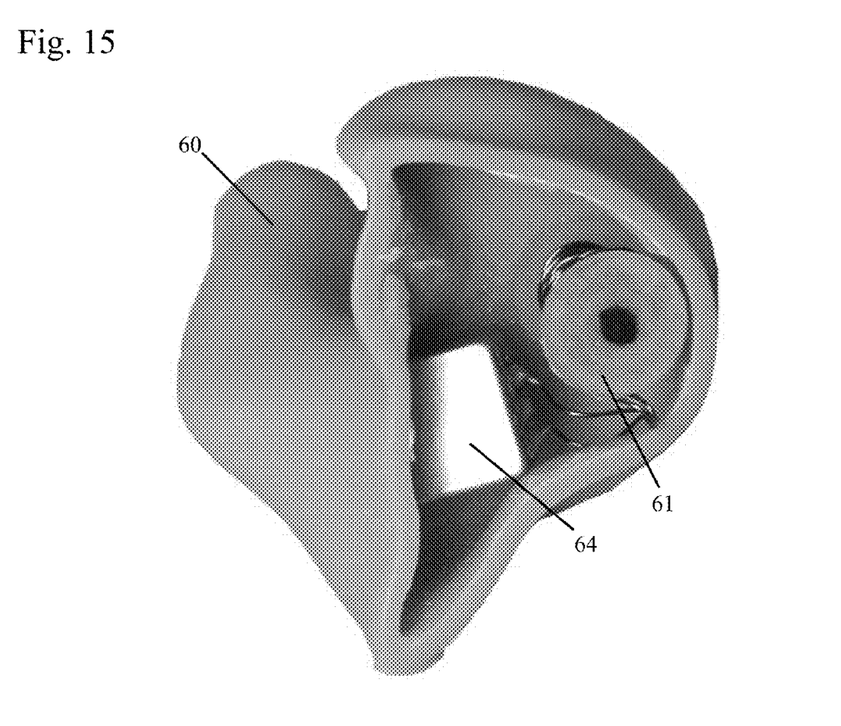
FIG. 15 shows an inside view of embodiment of FIG. 14

FIGS. 14 and 15 show an embodiment of the invention (without transmitter) using a custom molded earshell (60). The user's concha/canal geometry is determined from an impression or scanning or other technique, and a shell of either hard or malleable material is made. A receiver (61) is made of wire wrapped around a bobbin, with a core (62) of magnetic material such as magnetic ceramic or magnetic metal inside the bobbin. Wire (63) from the receiver is attached to a speaker (64).

The speaker (64) and receiver (61) are placed within the custom molded earshell (60). The earshell cavity may be filled. Tubing within the earshell acoustically couples the speaker (64) to the sound exit (65) of the earshell (60). In this way, sound is delivered from the speaker (64) to the ear canal.

It will be understood by one skilled in the art that the device can be used in helmets and other headgear without the use of earmuffs. In such a design, the transmitter would simply be mounted to the inside of the helmet, located so that it surrounds the pinna of the user's ear.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A communications system comprising:
   a loop transmitter comprising a coil of wire; and
   an earplug to insert into an ear of a user, the earplug comprising:
      a receiver including a wire; and
      a speaker coupled to the wire of the receiver;
   such that when the earplug is placed in a user's ear and the loop transmitter is placed near the a pinna of the user's ear, and an audio electrical signal is introduced into the coil of wire of the loop transmitter, a magnetic flux is created which is inductively coupled to the wire of the receiver and converted into an electrical voltage, the voltage driving the speaker to provide sound into the user's ear.

2. The system of claim 1, further comprising an earmuff for surrounding the user's ear.

3. The system of claim 2, in which the loop transmitter is mounted within the earmuff.

4. The system of claim 1, in which the loop transmitter is mounted within a helmet, located so that the loop transmitter is near the pinna of the user's ear.

5. The system of claim 1, in which the receiver further comprises a core of magnetic material within the wire of the receiver.

6. The system of claim 1, in which the speaker further comprises a case of magnetic material.

7. The system of claim 1 in which the earplug comprises an earshell having a body for insertion into a user's ear, in which the receiver and the speaker are located with the speaker mounted to direct sound into the ear.

8. The system of claim 1, in which the earplug further comprises an equalization circuit coupled to the receiver and to the speaker.

9. A communications headset comprising a pair of earmuffs for surrounding the user's ears, each earmuff comprising:
   a loop transmitter mounted within each earmuff, comprising:
      a receiver with electrical output at the ends of a wire; and
      a speaker coupled to the wire of the receiver,
   wherein when the earplug is placed in the user's ear, the headset is put on the user's head such that the at least one loop transmitter is placed near a pinna of the user's ear, and an audio electrical signal is introduced into the coil of wire of the loop transmitter, a magnetic flux is created which is inductively coupled to the receiver and converted into an electrical voltage, the electrical voltage driving the speaker to provide sound into the user's ear.

10. The headset of claim 9, in which each earmuff further comprises an ear cushion and the at least one loop transmitter is mounted within the ear cushion.

11. The headset of claim 10, in which the receiver further comprises a core of magnetic material.

12. The headset of claim 10, in which the speaker further comprises a case of magnetic material.

13. The headset of claim 10, in which the earplug comprises an earshell having a body for insertion into a user's ear, in which the receiver and the speaker are located with the speaker mounted to direct sound into the ear.

14. The headset of claim 10, in which the earplug further comprises an equalization circuit coupled to the receiver and to the speaker.

15. The headset of claim 10, further comprising a boom microphone attached to the headset.

16. A communications system comprising:
a loop transmitter comprising a coil of wire; and
an earplug comprising:
 a receiver that includes a coil of wire; and
 a speaker coupled to the coil of wire of the receiver,
wherein the communications system is configured to receiver a first audio communications signal input to the coil of wire of the loop transmitter, and generate a second audio communications signal output from the speaker.

17. The communications system of claim 16, wherein a passive electronic circuit is coupled to the receiver and to the speaker.

18. The communication system of claim 17, wherein the passive electronic circuit is a passive equalization circuit.

19. The communications system of claim 18, wherein the passive equalization circuit is a capacitor.

* * * * *